(12) United States Patent
Mehta et al.

(10) Patent No.: US 10,793,923 B2
(45) Date of Patent: Oct. 6, 2020

(54) COMPOSITIONS AND METHODS FOR DETECTION OF BK VIRUS

(71) Applicant: Roche Molecular Systems, Inc., Pleasanton, CA (US)

(72) Inventors: Rochak Mehta, Fremont, CA (US); Jingtao Sun, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/726,732

(22) Filed: Oct. 6, 2017

(65) Prior Publication Data

US 2018/0127838 A1    May 10, 2018

Related U.S. Application Data

(60) Provisional application No. 62/419,853, filed on Nov. 9, 2016.

(51) Int. Cl.
*C12Q 1/70*      (2006.01)
*C12Q 1/686*     (2018.01)
*G01N 33/569*    (2006.01)

(52) U.S. Cl.
CPC .......... *C12Q 1/701* (2013.01); *C12Q 1/686* (2013.01); *G01N 33/56983* (2013.01); *C12N 2710/22011* (2013.01); *C12Q 2600/16* (2013.01); *G01N 2333/025* (2013.01); *Y02A 50/30* (2018.01)

(58) Field of Classification Search
CPC combination set(s) only.
See application file for complete search history.

(56) References Cited

U.S. PATENT DOCUMENTS

| | | | |
|---|---|---|---|
| 7,892,795 B2 | 2/2011 | Chen et al. | |
| 8,748,092 B2 | 6/2014 | Chen et al. | |
| 9,745,638 B2 | 8/2017 | Chen et al. | |
| 2008/0318210 A1 | 12/2008 | Bentwich | |
| 2009/0246754 A1 | 10/2009 | Kiefer et al. | |
| 2014/0349275 A1 | 11/2014 | Chen et al. | |
| 2016/0244834 A1* | 8/2016 | Ong | C12Q 1/6883 |
| 2016/0281141 A1* | 9/2016 | Kim | C12Q 1/689 |

FOREIGN PATENT DOCUMENTS

| | | | |
|---|---|---|---|
| CN | 102344970 A | * | 2/2012 |
| EP | 1910578 B1 | | 6/2015 |
| WO | 2009105212 A2 | | 8/2009 |
| WO | 2011098484 A1 | | 8/2011 |

OTHER PUBLICATIONS

Mbianda, et al., Mechanisms of BK virus infection of renal cells and therapeutic implications, Journal of Clinical Virology 71:59-62 (2015).
Chen, et al., "Analysis of 15 novel full-length BK virus sequences from three individuals: evidence of a high intra-stain genetic diversity," Journal of General Biology 85:2651-2663 (2004).
Whiley, et al., "Detection and Differentiation of Human Polyomaviruses JC and BK by LightCycler PCR," Journal of Clinical Microbiology 39(12):4357-4361 (2001).
International Searching Authority, Notification of Transmittal of the International Search Report and the Written Opinion of the International Searching Authority, or Declaration; and International Search Report for PCT/EP2017/076832 (dated Jan. 10, 2018).
International Searching Authority, Written Opinion of the International Searching Authority for PCT/EP2017/076832 (dated Jan. 10, 2018).

* cited by examiner

*Primary Examiner* — Steven Pohnert
(74) *Attorney, Agent, or Firm* — Eric Grant Lee

(57) ABSTRACT

Methods for the rapid detection of the presence or absence of BK virus in a biological or non-biological sample are described. The methods can include performing an amplifying step, a hybridizing step, and a detecting step. Furthermore, primers and probes targeting BK virus and kits are provided that are designed for the detection of BK virus.

6 Claims, 7 Drawing Sheets

Specification includes a Sequence Listing.

US 10,793,923 B2

COMPOSITIONS AND METHODS FOR DETECTION OF BK VIRUS

CROSS REFERENCE TO RELATED APPLICATIONS

This application claims the benefit of priority of U.S. Provisional Patent Application No. 62/419,853, filed Nov. 10, 2016, which is incorporated herein by reference in its entirety.

FIELD OF THE INVENTION

The present disclosure relates to the field of in vitro viral diagnostics. Within this field, the present invention concerns the amplification and detection of a target nucleic acid that may be present in a sample and particularly, the amplification, detection, and quantitation of a target nucleic acid comprising sequence variations and/or individual mutations of BK virus, using primers and probes. The invention further provides reaction mixtures and kits containing primers and probes for amplification and detection of BK virus.

BACKGROUND OF THE INVENTION

BK virus, a member of the Polyomaviridae family, was first isolated in 1971 from the urine of a renal transplant recipient with ureteric stenosis, having the initials "B.K." The Polyomaviridae family includes John Cunningham virus (JCV) and simian virus SV40. Although BK virus infections are widespread, infected individuals are usually asymptomatic or exhibit only mild symptoms (e.g., respiratory infection or fever). The BK virus is a circular, double-stranded DNA virus. Its genome encodes three capsid structural proteins (i.e., viral capsid protein 1 (VP1), VP2, and VP3), as well as the large T and small t antigens.

After primary infection, the virus typically establishes latency in the uroepithelium and renal tubular epithelial cells. It is believed that up to 80% of the population contains a latent form of this virus. The symptoms of a BK virus infection for individuals who are immunosuppressed and/or immunocompromised, are significantly more severe, for example, in the setting of an organ transplant. In such case, clinical manifestations can include renal dysfunction and the presence of renal tubular cells and inflammatory cells in urine. In particular, in the setting of immunosuppression and/or immunocompromise, the virus reactivates and replicates, triggering a cascade of events starting with tubular cell lysis and viruria. The virus then multiplies in the interstitium and crosses into the peritubular capillaries, causing viremia and eventually invading the allograft, leading to various tubulointerstitial lesions and BK nephropathy (BKVN). The BK virus contributes significantly to the increase in probability of graft loss. BK virus is a common post-transplant opportunistic viral infection, affecting roughly 15% of renal plant recipients in the first post-transplant year. If unaddressed, BK nephropathy will progress to allograft failure.

Though being immunosuppressed and/or immunocompromised remains the primary risk factor for BK virus infection, other risk factors include male gender, older recipient age, prior rejection episodes, degree of human leukocyte antigen mismatching, prolonged cold ischemia time, BK serostatus, and ureteral stent placement. Treatment options for symptomatic BK virus-infected individuals are limited and there is no effective prophylaxis. The cornerstone of treatment is simply reduction of immunosuppression, which increases the risk of allograft rejection. Antiviral drugs are also employed, but with inconsistent results. BK virus is now recognized as a chief cause of interstitial nephritis and allograft failure in renal transplant recipients.

BK virus infection is diagnosed by a BK virus blood test or a urine test for decoy cells. The presence of decoy sells is a sensitive measure, but has a low positive predictive value (29%) for the diagnosis of BK nephropathy (see, Mbianda, et al. Journal of Clinical Virology 71:59-62 (2015). Quantification of viral load in the plasma and urine with either viral DNA or mRNA has also been used to diagnose BK nephropathy. However, a transplant kidney biopsy remains the gold standard for diagnosing BK virus nephropathy.

In the field of molecular diagnostics, the amplification and detection of nucleic acids is of considerable significance. Such methods can be employed to detect any number of microorganisms, such as viruses and bacteria. The most prominent and widely-used amplification technique is the Polymerase Chain Reaction (PCR). Other amplification techniques include Ligase Chain Reaction, Polymerase Ligase Chain Reaction, Gap-LCR, Repair Chain Reaction, 3 SR, NASBA, Strand Displacement Amplification (SDA), Transcription Mediated Amplification (TMA), and Qβ-amplification.

Automated systems for PCR-based analysis often make use of a real-time detection of product amplification during the PCR process in the same reaction vessel. Key to such methods is the use of modified oligonucleotides carrying reporter groups or labels.

An estimated 80% of the population harbors the BK virus in a latent state, many of them unknowingly so, because the symptoms of a BK virus infection are so mild or nonexistent. The gold standard for diagnosing BK nephropathy is a transplant kidney biopsy, which is a time-consuming, invasive, and laborious procedure. Therefore, there is a need in the art for a quick, reliable, specific, and sensitive method for detecting and quantifying the presence of BK virus in a biological sample.

SUMMARY OF THE INVENTION

Certain embodiments in the present disclosure relate to methods for the rapid detection of the presence or absence of BK virus in a biological or non-biological sample, for example, multiplex detection and quantitating of BK virus by real-time polymerase chain reaction (PCR) in a single test tube or vessel. Embodiments include methods of detection of BK virus comprising performing at least one cycling step, which may include an amplifying step and a hybridizing step. Furthermore, embodiments include primers, probes, and kits that are designed for the detection of BK virus in a single tube or vessel.

One embodiment of the claimed invention is directed to a method of detecting BK Virus in a sample, the method comprising: (a) performing an amplifying step comprising contacting the sample with one or more set of primers to produce an amplification product, if a target nucleic acid of BK Virus is present in the sample; (b) performing a hybridization step comprising contacting the amplification product, if a target nucleic acid is present in the sample, with one or more probes; and (c) detecting the presence or absence of the amplification product, wherein the presence of the amplification product is indicative of the presence of BK Virus in the sample, and wherein the absence of the amplification product is indicative of the absence of BK Virus in the sample; wherein the one or more set of primers comprise at least two primers selected from a group consisting of SEQ ID NOs:1, 2, 4, 5, 6, 7, 9, and 10, or a complement thereof; and wherein the one or more probes are selected from a group consisting of SEQ ID NOs:3, 8, and 11, or a complement thereof. In a related embodiment, the one or more set of primers comprises two primers consisting of SEQ ID NOs:1 and 2, or a complement thereof, and the one or more probes comprises a probe consisting of SEQ ID NO:3, or a complement thereof. In a related embodiment, the one or more set of primers comprises two primers consisting of SEQ ID NOs:4 and 5, or a complement thereof, and the one or more probes comprises a probe consisting of SEQ ID NO:3, or a complement thereof. In a related embodiment, the one or more set of primers comprises two primers consisting of SEQ ID NOs:6 and 7, or a complement thereof, and the one or more probes comprises a probe consisting of SEQ ID NO:8, or a complement thereof. In a related embodiment, the one or more set of primers comprises two primers consisting of SEQ ID NOs:9 and 10, or a complement thereof, and the one or more probes comprises a probe consisting of SEQ ID NO:11, or a complement thereof. In other embodiment, the hybridization step comprises contacting the amplification product with the probe that is labeled with a donor fluorescent moiety and a corresponding acceptor moiety; the detecting step comprises detecting the presence or absence of fluorescence resonance energy transfer (FRET) between the donor fluorescent moiety and the acceptor moiety of the probe, and the presence or absence of fluorescence is indicative of the presence of absence of BK Virus in the sample. In another embodiment, the amplification step comprises a polymerase enzyme having 5' to 3' nuclease activity. In another embodiment, the acceptor moiety is a quencher, such as BlackHole Quencher™-2 (BHQ-2). In another embodiment, the donor fluorescent moiety is HEX. In another embodiment, the sample is a biological sample, which includes, but is not limited to, blood, plasma, or urine. In yet another embodiment, the method further comprises detecting, in in parallel, a second target nucleic acid from one or more other microorganisms. In a related embodiment, the one or more other microorganisms is a bacteria. In a related embodiment, the one or more other microorganisms is a virus, including, but not limited to, Hepatitis A Virus (HAV), Hepatitis B Virus (HBV), Hepatitis C Virus (HCV), Hepatitis E Virus (HEV), Human Immunodeficiency Virus (HIV), West Nile Virus (WNV), Japanese Encephalitis Virus (JEV), Zika Virus, Dengue Fever Virus, St. Louis Encephalitis Virus (SLEV), and/or Chikungunya Virus.

Another embodiment of the claimed invention is directed a kit for detecting a nucleic acid of BK Virus comprising: (a) a set of primers comprising at least two primers selected from the a group consisting of SEQ ID NOs:1, 2, 4, 5, 6, 7, 9, and 10, or a complement thereof; and (b) one or more fluorescently detectably labeled probes selected from a group consisting of SEQ ID NOs:3, 8, and 11, or a complement thereof, wherein the fluorescently detectably labeled probe is configured to hybridize to an amplicon generated by the at least two primers. In a related embodiment, the set of primers comprises two primers consisting of SEQ ID NOs:1 and 2, or a complement thereof, and the one or more probes comprises a probe consisting of SEQ ID NO:3, or a complement thereof. In a related embodiment, the set of primers comprises two primers consisting of SEQ ID NOs:4 and 5, or a complement thereof, and the one or more probes comprises a probe consisting of SEQ ID NO:3, or a complement thereof. In a related embodiment, the set of primers comprises two primers consisting of SEQ ID NOs:6 and 7, or a complement thereof, and the one or more probes comprises a probe consisting of SEQ ID NO:8, or a complement thereof. In a related embodiment, the set of primers comprises two primers consisting of SEQ ID NOs:9 and 10, or a complement thereof, and the one or more probes comprises a probe consisting of SEQ ID NO:11, or a complement thereof. In another embodiment, the detectably labeled oligonucleotide sequence comprises a donor fluorescent moiety and a corresponding acceptor moiety. In one embodiment, the acceptor moiety is a quencher, such as BlackHole Quencher™-2 (BHQ-2). In another embodiment, the donor fluorescent moiety is HEX. In one embodiment, the sample is a biological sample, including, but not limited to, blood, plasma, or urine. In another embodiment, the kit further comprises primers and probes for the amplification and detection of a second target from one or more other microorganisms. In one embodiment, the one or more microorganisms is a bacteria. In one embodiment, the one or more other microorganisms is a virus, including, but not limited to, Hepatitis A Virus (HAV), Hepatitis B Virus (HBV), Hepatitis C Virus (HCV), Hepatitis E Virus (HEV), Human Immunodeficiency Virus (HIV), West Nile Virus (WNV), Japanese Encephalitis Virus (JEV), Zika Virus, Dengue Fever Virus, St. Louis Encephalitis Virus (SLEV), and/or Chikungunya Virus. In yet another embodiment, the kit further comprises nucleoside triphosphates, nucleic acid polymerase, and buffers necessary for the function of the nucleic acid polymerase. In another embodiment, the at least one of either the at least two primers or the fluorescently detectable labeled probe comprises at least one modified nucleotide.

Another embodiment of the claimed invention is directed to a set of primers and one or more probes for the detection of BK Virus in a sample, wherein the set of primers comprises at least two primers selected from a group consisting of SEQ ID NOs:1, 2, 4, 5, 6, 7, 9, and 10, or a complement thereof; and the one or more probes are selected from a group consisting of SEQ ID NOs:3, 8, and 11, or a complement thereof. In a related embodiment, the set of primers comprises two primers consisting of SEQ ID NOs:1 and 2, or a complement thereof, and the one or more probes comprises a probe consisting of SEQ ID NO:3, or a complement thereof. In a related embodiment, the set of primers comprises two primers consisting of SEQ ID NOs:4 and 5, or a complement thereof, and the one or more probes comprises a probe consisting of SEQ ID NO:3, or a complement thereof. In a related embodiment, the set of primers comprises two primers consisting of SEQ ID NOs:6 and 7, or a complement thereof, and the one or more probes comprises a probe consisting of SEQ ID NO:8, or a complement thereof. In a related embodiment, the set of primers comprises two primers consisting of SEQ ID NOs:9 and 10, or a complement thereof, and the one or more probes comprises a probe consisting of SEQ ID NO:11, or a complement thereof. In another embodiment, an amplifying step is performed comprising contacting a sample with the set of primers to produce an amplification product if a nucleic acid is present in the sample; performing a hybridization step comprising contacting the amplification product with the one or more probes; and detecting the presence or absence of the amplification product, wherein the presence of the amplification product is indicative of the presence of BK Virus in the sample and wherein the absence of the amplification product is indicative of the absence of BK Virus in the sample. In one embodiment, the hybridization step comprises contacting the amplification product with the probe that is labeled with a donor fluorescent moiety and a corresponding acceptor moiety; and the detecting step comprises detecting the presence or absence of FRET between the donor fluorescent moiety and the acceptor moiety of the probe, wherein the presence or absence of fluorescence is indicative of the presence or absence of BK Virus in the sample. In one embodiment, the amplification step comprises a polymerase enzyme having 5' to 3' nuclease activity. In another embodiment, the acceptor moiety is a quencher, such as BlackHole Quencher™-2 (BHQ-2). In one embodiment, the donor fluorescent moiety is HEX. In one embodiment, the sample is a biological sample, including, but not limited to blood, plasma, or urine.

Other embodiments provide an oligonucleotide comprising or consisting of a sequence of nucleotides selected from SEQ ID NOs:1-11, or a complement thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs:1-11, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 8 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

The present disclosure also provides for methods of detecting the presence or absence of BK virus or BK virus nucleic acid, in a biological sample from an individual. These methods can be employed to detect the presence or absence of BK virus nucleic acid in plasma, for use in blood screening and diagnostic testing. Additionally, the same test may be used by someone experienced in the art to assess urine and other sample types to detect and/or quantitate BK virus nucleic acid. Such methods generally include performing at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of BK virus nucleic acid in the sample, and wherein the absence of binding is indicative of the absence of BK virus nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of BK virus nucleic acid nucleic acid.

In a further embodiment, a kit for detecting and/or quantitating one or more nucleic acids of BK virus is provided. The kit can include one or more sets of primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of BK virus nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
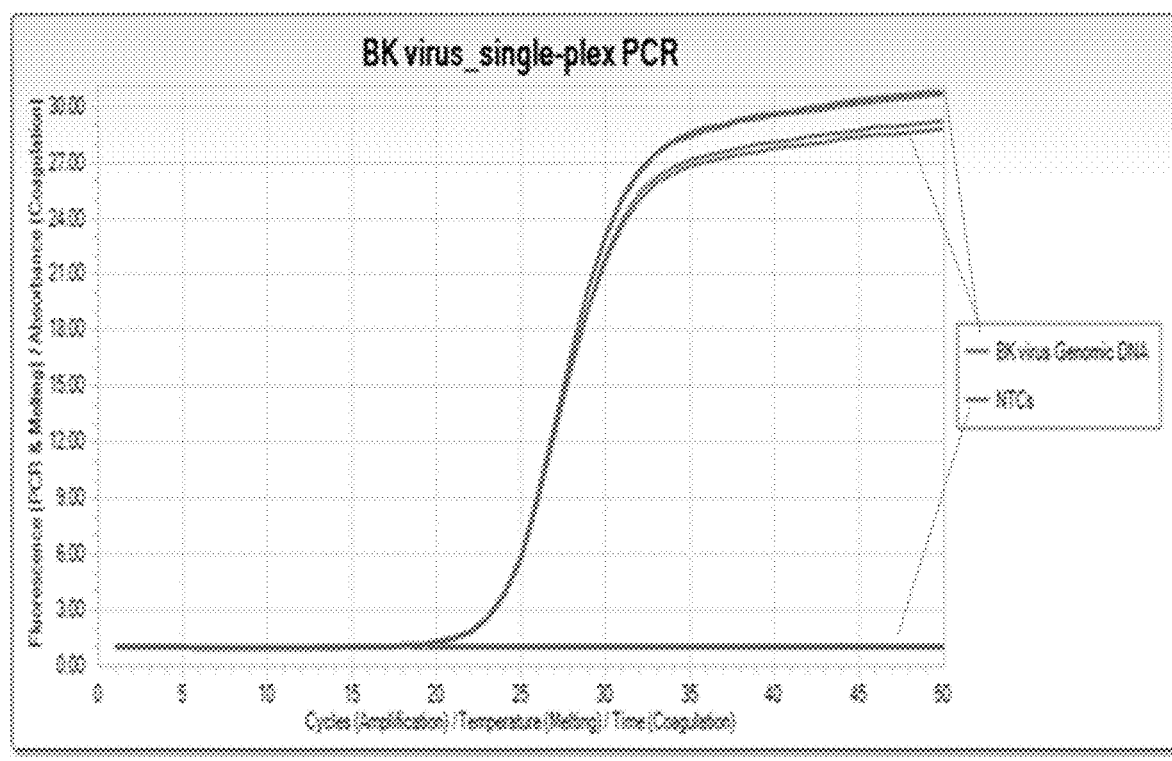
FIG. 1 shows real-time PCR growth curves showing the detection of BK virus genomic DNA samples ($4 \times 10^5$ genomes/µl) by primers (SEQ ID NOs:4 and 5) and probe (SEQ ID NO:3) specific for BK virus.

Diagnosis of BK virus infection by nucleic acid amplification provides a method for rapidly, accurately, reliably, specifically, and sensitively detecting and/or quantitating the BK viral infection. A real-time PCR assay for detecting and/or quantitating BK virus in a non-biological or biological sample is described herein. Primers and probes for detecting and/or quantitating BK virus are provided, as are articles of manufacture or kits containing such primers and probes. The increased specificity and sensitivity of real-time PCR for detection of BK virus compared to other methods, as well as the improved features of real-time PCR including sample containment and real-time detection and quantitating of the amplified product, make feasible the implementation of this technology for routine diagnosis of BK virus infections in the clinical laboratory. Additionally, this technology may be employed for blood screening as well as for prognosis. This BK virus detection assay may also be multiplexed with other assays for the detection of other nucleic acids, e.g., other bacteria and/or viruses, in parallel.

The present disclosure includes oligonucleotide primers and fluorescent labeled hydrolysis probes that hybridize to the BK virus genome, in order to specifically identify BK virus using, e.g., TaqMan® amplification and detection technology.

The disclosed methods may include performing at least one cycling step that includes amplifying one or more portions of the nucleic acid molecule gene target from a sample using one or more pairs of primers. "BK primer(s)" as used herein refer to oligonucleotide primers that specifically anneal to nucleic acid sequences found in the BK virus genome, and initiate DNA synthesis therefrom under appropriate conditions producing the respective amplification products. Examples of nucleic acid sequences found in the BK virus genome, include nucleic acids within viral capsid protein region of the BK virus genome, such as the VP2 region. Each of the discussed BK virus primers anneals to a target such that at least a portion of each amplification product contains nucleic acid sequence corresponding to the target. The one or more amplification products are produced provided that one or more nucleic acid is present in the sample, thus the presence of the one or more amplification products is indicative of the presence of BK virus in the sample. The amplification product should contain the nucleic acid sequences that are complementary to one or more detectable probes for BK virus. "BK virus probe(s)" as used herein refer to oligonucleotide probes that specifically anneal to nucleic acid sequences found in the BK virus genome. Each cycling step includes an amplification step, a hybridization step, and a detection step, in which the sample is contacted with the one or more detectable BK virus probes for detection of the presence or absence of BK virus in the sample.

As used herein, the term "amplifying" refers to the process of synthesizing nucleic acid molecules that are complementary to one or both strands of a template nucleic acid molecule (e.g., nucleic acid molecules from the BK virus genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, a 5-propynyl dU, a 5-propynyl dC, 7-deaza-deoxyguanosine (deaza G (u-deaza)) and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection/Quantitation of BK Virus Target Nucleic Acid

The present disclosure provides methods to detect BK virus by amplifying, for example, a portion of the BK virus nucleic acid sequence. Specifically, primers and probes to amplify and detect and/or quantitate BK virus nucleic acid molecule targets are provided by the embodiments in the present disclosure.

For detection and/or quantitation of BK virus, primers and probes to amplify and detect/quantitate the BK virus are provided. BK virus nucleic acids other than those exemplified herein can also be used to detect BK virus in a sample. For example, functional variants can be evaluated for specificity and/or sensitivity by those of skill in the art using routine methods. Representative functional variants can include, e.g., one or more deletions, insertions, and/or substitutions in the BK virus nucleic acids disclosed herein.

More specifically, embodiments of the oligonucleotides each include a nucleic acid with a sequence selected from SEQ ID NOs:1-11, a substantially identical variant thereof in which the variant has at least, e.g., 80%, 90%, or 95% sequence identity to one of SEQ ID NOs:1-11, or a complement of SEQ ID NOs:1-11 and the variant.

TABLE 1

BK Virus Oligonucleotides

| Oligo Type | SEQ ID NO: | Sequence | Modifications |
|---|---|---|---|
| Forward Primer | 1 | CCTAACTCCTCAAACATATGCTGTJ | J: t-Butyl Benzyl-dA |
| Reverse Primer | 2 | ACAGTGGAAACTTTGTGATCCCJ | J: t-Butyl Benzyl-dA |
| Probe | 3 | HATTGCQTGGTGCTCCTGZGGCTATTGCTP | H: HEX-Thr<br>Z: 7-deaza-deoxyguanosine<br>Q: BHQ-2<br>P: Phosphate |

TABLE 1-continued

BK Virus Oligonucleotides

| Oligo Type | SEQ ID NO: | Sequence | Modifications |
|---|---|---|---|
| Forward Primer | 4 | GGCTATAGCTGCTATAGGCCTAJ | J: t-Butyl Benzyl-dA |
| Reverse Primer | 5 | AGTAACAGTTTGAATTAAAGCAGCAAAK | K: t-Butyl Benzyl-dC |
| Forward Primer | 6 | AGAGGAAAATCAGCACAAACCTK | K: t-Butyl Benzyl-dC |
| Reverse Primer | 7 | CACCCTGACAAAGGGGGK | K: t-Butyl Benzyl-dC |
| Probe | 8 | HTGAGCTAQCTCCAGGTTCCAAAATCAGGCTGATGAP | H: HEX-Thr<br>Q: BHQ-2<br>P: Phosphate |
| Forward Primer | 9 | CCTTTACATCCTGCTCCATTTTTTTATJ | J: t-Butyl Benzyl-dA |
| Reverse Primer | 10 | AGTGTAAGGAATTTCACCCTGACJ | J: t-Butyl Benzyl-dA |
| Probe | 11 | HAGTATTCQATTCTCTTCATTTTATCCTCGTCGCCCCCTTP | H: HEX-Thr<br>Q: BHQ-2<br>P: Phosphate |

In one embodiment, the above described sets of BK virus primers and probes are used in order to provide for detection of BK virus in a biological sample suspected of containing BK virus (Table 1). The sets of primers and probes may comprise or consist of the primers and probes specific for the BK virus nucleic acid sequences, comprising or consisting of the nucleic acid sequences of SEQ ID NOs:1-11. In another embodiment, the primers and probes for the BK virus target comprise or consist of a functionally active variant of any of the primers and probes of SEQ ID NOs:1-11.

A functionally active variant of any of the primers and/or probes of SEQ ID NOs:1-11 may be identified by using the primers and/or probes in the disclosed methods. A functionally active variant of a primer and/or probe of any of the SEQ ID NOs:1-11 pertains to a primer and/or probe which provide a similar or higher specificity and sensitivity in the described method or kit as compared to the respective sequence of SEQ ID NOs:1-11.

The variant may, e.g., vary from the sequence of SEQ ID NOs:1-11 by one or more nucleotide additions, deletions or substitutions such as one or more nucleotide additions, deletions or substitutions at the 5' end and/or the 3' end of the respective sequence of SEQ ID NOs:1-11. As detailed above, a primer and/or probe may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the BK virus target, e.g., nucleic acids encoding alternative portions of BK virus can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of BK virus. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a BK virus (target) nucleic acid. A "probe" can be referred to as a "detection probe" meaning that it detects the target nucleic acid.

In some embodiments, the described BK virus probes can be labeled with at least one fluorescent label. In one embodiment, the BK virus probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NO:3, 8 or 11.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of BK virus primers and probes nucleic acid molecules (e.g., SEQ ID NOs:1, 2, 3, 4, 5, 6, 7, 8, 9, 10, and 11). Constructs can be used, for example, as control template nucleic acid molecules. Vectors suitable for use are commercially available and/or produced by recombinant nucleic acid technology methods routine in the art. BK virus nucleic acid molecules can be obtained, for example, by chemical synthesis, direct cloning from BK virus, or by nucleic acid amplification.

Constructs suitable for use in the methods typically include, in addition to the BK virus nucleic acid molecules (e.g., a nucleic acid molecule that contains one or more sequences of SEQ ID NOs:1-11), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing BK virus nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described BK virus nucleic acid sequences (e.g., SEQ ID NOs:1, 2, 4-7, 9, and 10). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ BK virus nucleic acid such as RNA or DNA (cDNA). The template nucleic acid need not be purified; it may be a minor fraction of a complex mixture, such as BK virus nucleic acid contained in human cells. BK virus nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs:1, 2, 4, 5, 6, 7, 9, and 10) are combined with PCR reagents under reaction conditions that induce primer extension. For example, chain extension reactions generally include 50 mM KCl, 10 mM Tris-HCl (pH 8.3), 15 mM $MgCl_2$, 0.001%

(w/v) gelatin, 0.5-1.0 µg denatured template DNA, 50 pmoles of each oligonucleotide primer, 2.5 U of Taq polymerase, and 10% DMSO). The reactions usually contain 150 to 320 each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target BK virus nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety (e.g., HEX) and a corresponding quencher (e.g., BlackHole Quencher™ (BHQ) (such as BHQ-2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quencher™ (BHQ) (such as BHQ2), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the BK virus target nucleic acid sequence. Upon hybridization of the oligonucleotide probes to the amplification product nucleic acid at the appropriate positions, a FRET signal is generated.

Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimidyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of BK Virus Amplified Product (Amplicon)

The present disclosure provides methods for detecting the presence or absence of BK virus in a biological or non-biological sample. Methods provided avoid problems of sample contamination, false negatives, and false positives. The methods include performing at least one cycling step that includes amplifying a portion of BK virus target nucleic acid molecules from a sample using one or more pairs of BK virus primers, and a FRET detecting step. Multiple cycling steps are performed, preferably in a thermocycler. Methods can be performed using the BK virus primers and probes to detect the presence of BK virus, and the detection of BK virus indicates the presence of BK virus in the sample.

As described herein, amplification products can be detected using labeled hybridization probes that take advantage of FRET technology. One FRET format utilizes TaqMan® technology to detect the presence or absence of an amplification product, and hence, the presence or absence of BK virus. TaqMan® technology utilizes one single-stranded hybridization probe labeled with, e.g., one fluorescent dye (e.g., HEX) and one quencher (e.g., BHQ-2), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product, or amplicon) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of BK virus in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of BK virus genomes). If amplification of BK virus target nucleic acid occurs and an amplification product is produced, the step of hybridizing results in a detectable signal based upon FRET between the members of the pair of probes.

Generally, the presence of FRET indicates the presence of BK virus in the sample, and the absence of FRET indicates the absence of BK virus in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to respiratory specimens, urine, fecal specimens, blood specimens, plasma, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release BK virus nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the BK virus probes from the BK virus amplification products can confirm the presence or absence of BK virus in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect BK virus. An article of manufacture can include primers and probes used to detect the BK virus gene target, together with suitable packaging materials. Representative primers and probes for detection of BK virus are capable of hybridizing to BK virus target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to BK virus target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the BK virus probes. Examples of suitable FRET donor fluorescent moieties and corresponding acceptor fluorescent moieties are provided above.

Articles of manufacture can also contain a package insert or package label having instructions thereon for using the BK virus primers and probes to detect BK virus in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure also provide for a set of primers and one or more detectable probes for the detection of BK virus in a sample.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

The targeted region of the BK virus genome was the VP2 region of the BK virus genome. All nucleic acid sequences were aligned and all primers and probes were considered and scored for their predicted inclusivity for all known BK virus isolates and other properties.

Example 1: Specificity of Real-Time BK Virus PCR (SEQ ID NOs:3-5)

BK virus genomic DNA samples were used for a single-plex real-time PCR assay at a concentration of $4.0 \times 10^5$ BK virus genome/µl. Reagents used include cobas® 6800/8800 generic PCR Master Mix, with the profile and conditions for use with the cobas® 6800/8800, and using TaqMan® amplification and detection technology. The final concentration of oligonucleotides in the master mix ranged from 0.10-0.40 µM. The cobas® 6800/8800 PCR Profile employed is depicted in Table 2, below:

TABLE 2

| cobas ® 6800/8800 PCR Profile | | | | |
|---|---|---|---|---|
| Step | Cycles | Target (° C.) | Hold time (hh:mm:ss) | Ramp |
| Pre-PCR | 1 | 50 | 00:02:00 | 4.4 |
| | | 94 | 00:00:05 | 4.4 |
| | | 55 | 00:02:00 | 2.2 |

TABLE 2-continued cobas® 6800/8800 PCR Profile

| Step | Cycles | Target (° C.) | Hold time (hh:mm:ss) | Ramp |
|---|---|---|---|---|
|  |  | 60 | 00:06:00 | 4.4 |
|  |  | 65 | 00:04:00 | 4.4 |
| 1. Meas | 5 | 95 | 00:00:05 | 4.4 |
|  |  | 55 | 00:00:30 | 2.2 |
| 2. Meas | 45 | 91 | 00:00:05 | 4.4 |
|  |  | 58 | 00:00:25 | 2.2 |
| Post | 1 | 40 | 00:02:00 | 2.2 |

The oligonucleotides specific for BK virus used for the real-time PCR assay were SEQ ID NO:4 for the forward primer, SEQ ID NO:5 for the reverse primer, and SEQ ID NO:3 for the probe. These oligonucleotides target the VP2 region of the BK virus genome. The probe used in these examples is a TaqMan® probe.

Figure 2:
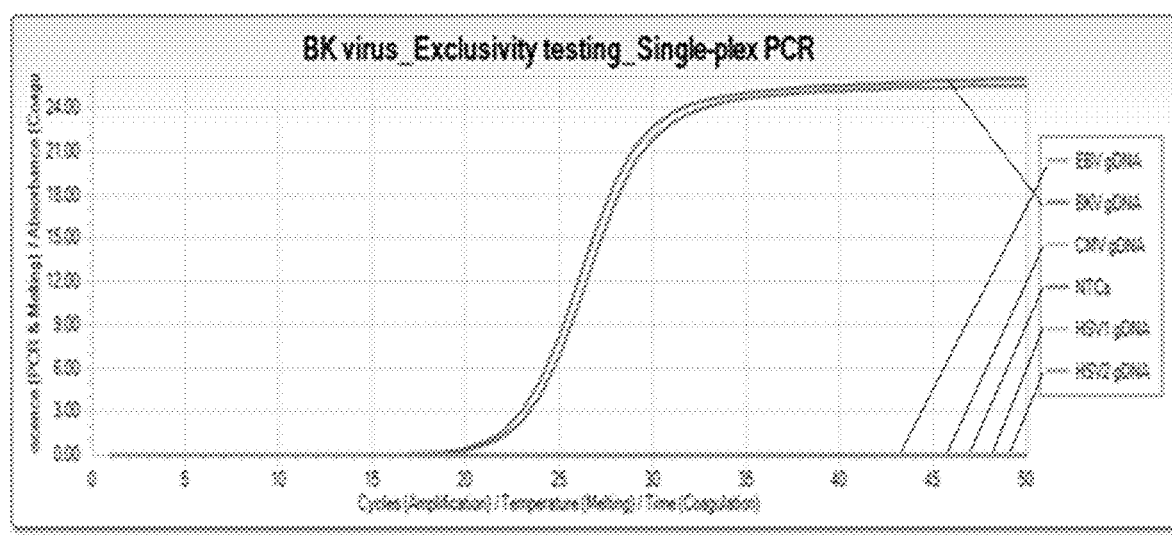
FIG. 2 shows real-time PCR growth curves showing the specific detection of BK virus genomic DNA samples ($4 \times 10^5$ genomes/µl) by primers (SEQ ID NOs:4 and 5) and probe (SEQ ID NO:3). BK virus primers and probes are not cross-reactive with genomic DNA from other viral DNA samples from Epstein Barr Virus (EBV), Herpes Simplex Virus-1 (HSV-1), HSV-2, and Cytomegalovirus (CMV), tested at $1\times10^8$ copies/µl. No signal was observed for the genomic DNA samples other than BK virus.

The results of the real-time BK virus assay are shown in FIG. 1, which shows real-time PCR growth curves. Additionally, real-time PCR studies were conducted in the presence of genomic DNA from other viruses, to confirm specificity of the BK virus and lack of cross reactivity. The results, shown in FIG. 2, demonstrate that the BK virus primers (SEQ ID NOs:4 and 5) and probe (SEQ ID NO:3) are specific for BK virus and do not cross react with genomic DNA from other viral samples (tested at $1\times10^8$ copies/µl) from Epstein Barr Virus (EBV), Herpes Simplex Virus-1 (HSV-1), HSV-2, or cytomegalovirus (CMV). No signal was observed for the genomic DNA samples, other than BK virus.

Thus, these results demonstrate that the primers and probes (SEQ ID NOs:3-5) amplify and detect the presence of BK virus specifically in a real-time PCR assay.

Example 2: Sensitivity of Real-Time BK Virus PCR (SEQ ID NOs:1-3)

BK virus genomic DNA samples were used for a real-time PCR assay at a varying concentrations, with a dilution panel including $1\times10^1$ genomes/µl, $1\times10^2$ genomes/µl, $1\times10^3$ genomes/µl, $1\times10^4$ genomes/µl, $1\times10^5$ genomes/µl, and $4\times10^5$ genomes/µl. Reagents used include cobas® 6800/8800 generic PCR Master Mix, with the profile and conditions for use with the cobas® 6800/8800, and using TaqMan® amplification and detection technology. The final concentration of oligonucleotides in the master mix ranged from 0.10-0.40 µM. The cobas® 6800/8800 PCR Profile employed is depicted in Table 2, above.

The primers specific for BK virus used for this real-time PCR assay were different than the ones employed in Example 1. Here, the oligonucleotides were SEQ ID NO:1 for the forward primer, SEQ ID NO:2 for the reverse primer, and SEQ ID NO:3 for the probe. These oligonucleotides target the VP2 region of the BK virus genome. The probe used in these examples is a TaqMan® probe.

Figure 3:
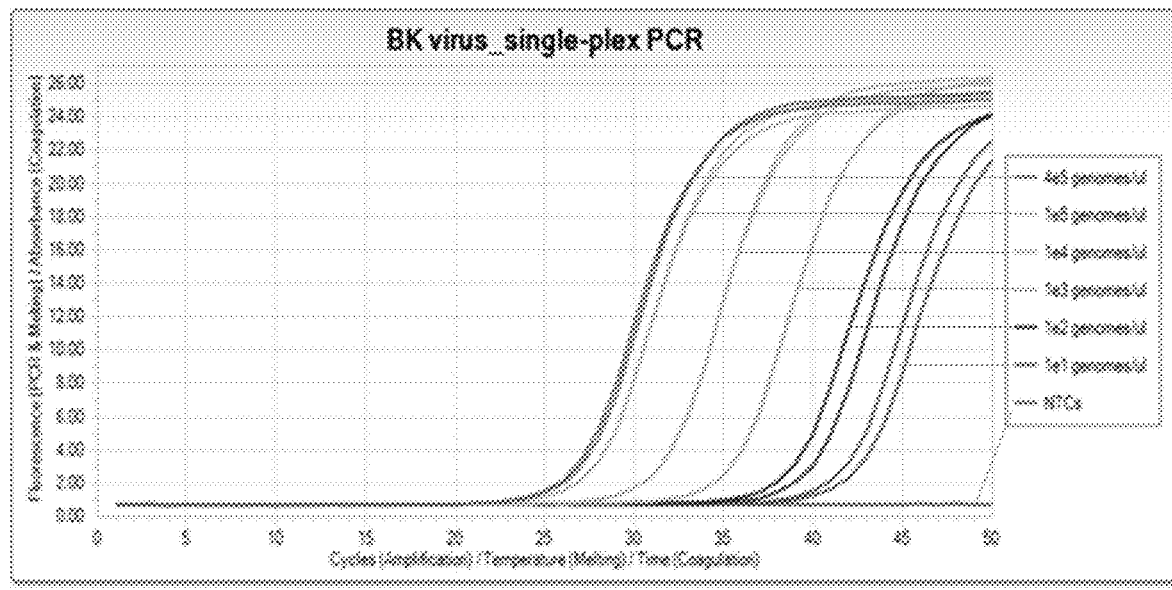
FIG. 3 shows real-time PCR growth curves showing the sensitivity of detection of BK virus genomic DNA samples by primers (SEQ ID NOs:1 and 2) and probe (SEQ ID NO:3). A dilution panel was employed with DNA samples at the following varying concentrations: $1\times10^1$ genomes/µl, $1\times10^2$ genomes/µl, $1\times10^3$ genomes/µl, $1\times10^4$ genomes/µl, $1\times10^5$ genomes/µl, and $4\times10^5$ genomes/µl. Results demonstrate the sensitivity of the primers and probes, showing the ability to detect BK virus DNA at levels as low as $1\times10^1$ genomes/µl.

The results of the real-time BK virus assay are shown in FIG. 3, which shows real-time PCR growth curves of the dilution panel. These results show that the primers (SEQ ID NOs:1 and 2) and probe (SEQ ID NO:3) amplify and detect BK virus in a dose-dependent fashion.

Thus, these results demonstrate the sensitivity of the primers and probes (SEQ ID NOs:1-3) in amplifying and detecting the presence of BK virus in a real-time PCR assay. The results indicate that the primers (SEQ ID NOs:1 and 2) and probe (SEQ ID NO:3) can achieve a sensitivity down to $1\times10^1$ genomes/µl.

Example 3: Sensitivity of Real-Time BK Virus PCR (SEQ ID NOs:6-8)

BK virus genomic DNA samples were used for a real-time PCR assay at a varying concentrations, with a dilution panel including $1\times10^1$ genomes/µl, $1\times10^2$ genomes/µl, and $1\times10^3$ genomes/µl. Reagents used include cobas® 6800/8800 generic PCR Master Mix, with the profile and conditions for use with the cobas® 6800/8800, and using TaqMan® amplification and detection technology. The final concentration of oligonucleotides in the master mix ranged from 0.10-0.40 µM. The cobas® 6800/8800 PCR Profile employed is depicted in Table 2, above.

The oligonucleotides specific for BK virus used for the real-time PCR assay were SEQ ID NO:6 for the forward primer, SEQ ID NO:7 for the reverse primer, and SEQ ID NO:8 for the probe. These oligonucleotides target the small t-antigen region of the BK virus genome. The probe used in these examples is a TaqMan® probe.

Figure 4:
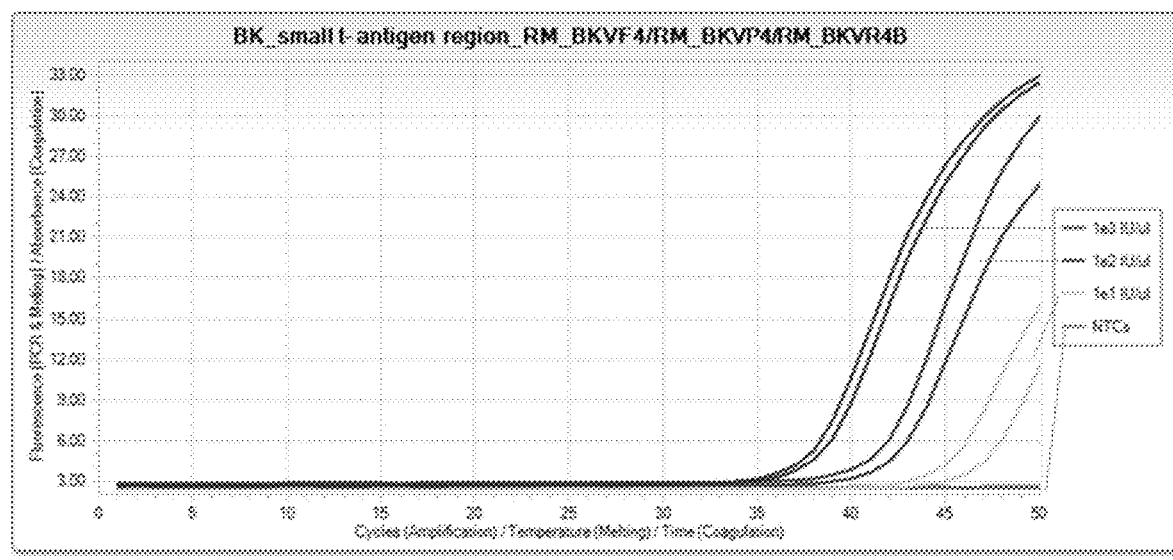
FIG. 4 shows real-time PCR growth curves showing the sensitivity of detection of BK virus genomic DNA samples by primers (SEQ ID NOs:6 and 7) and probe (SEQ ID NO:8). A dilution panel was employed with DNA samples at the following varying concentrations: $1\times10^1$ genomes/µl, $1\times10^2$ genomes/µl, and $1\times10^3$ genomes/µl. Results demonstrate the sensitivity of the primers and probes, showing the ability to detect BK virus DNA at levels as low as $1\times10^1$ genomes/µl

The results of the real-time BK virus assay are shown in FIG. 4, which shows real-time PCR growth curves of the dilution panel. These results show that the primers (SEQ ID NOs:6 and 7) and probe (SEQ ID NO:8) amplify and detect BK virus in a dose-dependent fashion.

Thus, these results demonstrate the sensitivity of the primers and probes (SEQ ID NOs:6-8) in amplifying and detecting the presence of BK virus in a real-time PCR assay. The results indicate that the primers (SEQ ID NOs:6 and 7) and probe (SEQ ID NO:8) can achieve a sensitivity down to $1\times10^1$ genomes/µl.

Example 4: Sensitivity of Real-Time BK Virus PCR (SEQ ID NOs:9-11)

BK virus genomic DNA samples were used for a real-time PCR assay at a varying concentrations, with a dilution panel including $1\times10^1$ genomes/µl, $1\times10^2$ genomes/µl, and $1\times10^3$ genomes/µl. Reagents used include cobas® 6800/8800 generic PCR Master Mix, with the profile and conditions for use with the cobas® 6800/8800, and using TaqMan® amplification and detection technology. The final concentration of oligonucleotides in the master mix ranged from 0.10-0.40 µM. The cobas® 6800/8800 PCR Profile employed is depicted in Table 2, above.

The oligonucleotides specific for BK virus used for the real-time PCR assay were SEQ ID NO:9 for the forward primer, SEQ ID NO:10 for the reverse primer, and SEQ ID NO:11 for the probe. These oligonucleotides target the small t-antigen region of the BK virus genome. The probe used in these examples is a TaqMan® probe.

Figure 5:
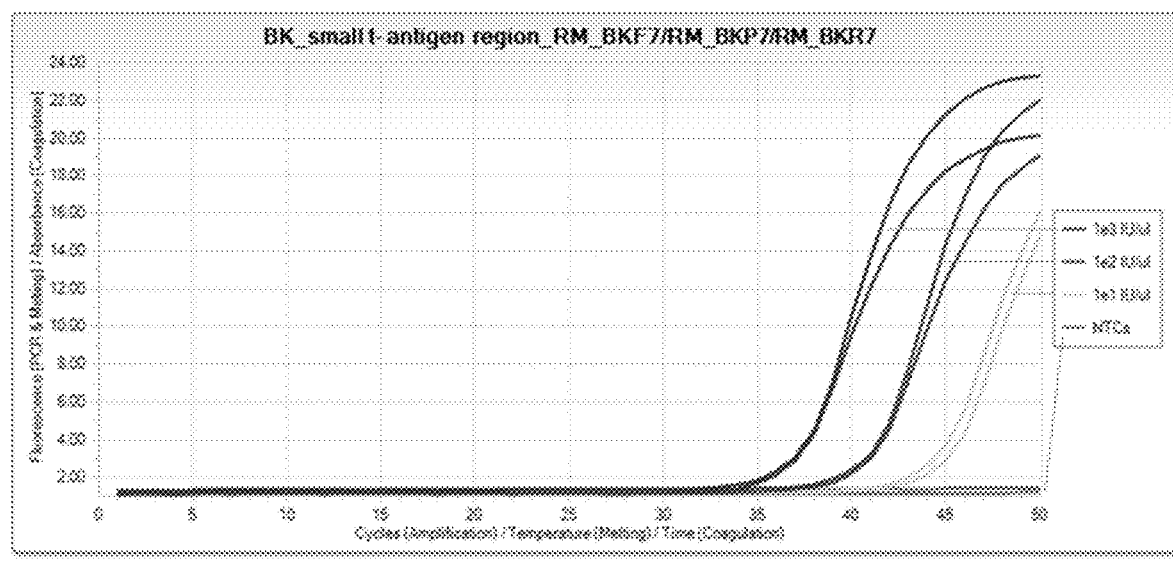
FIG. 5 shows real-time PCR growth curves showing the sensitivity of detection of BK virus genomic DNA samples by primers (SEQ ID NOs:9 and 10) and probe (SEQ ID NO:11). A dilution panel was employed with DNA samples at the following varying concentrations: $1\times10^1$ genomes/µl, $1\times10^2$ genomes/µl, and $1\times10^3$ genomes/µl. Results demonstrate the sensitivity of the primers and probes, showing the ability to detect BK virus DNA at levels as low as $1\times10^1$ genomes/µl.

The results of the real-time BK virus assay are shown in FIG. 5, which shows real-time PCR growth curves of the dilution panel. These results show that the primers (SEQ ID NOs:9 and 10) and probe (SEQ ID NO:11) amplify and detect BK virus in a dose-dependent fashion.

Example 5: Dual Target Multiplex Real-Time BK Virus PCR (SEQ ID NOs:3-5 and SEQ ID NOs:6-8)

The oligonucleotides were tested in a multiplex real-time PCR assay, such that two targets (i.e., "dual target") were tested (i.e., VP2 and small t-antigen). In this test, the BK virus standards were obtained from the Exact Diagnostics BKV Verification Panel (Exact Diagnostics (EDX), Catalog Number BKVP100). The EDX BKV Verification Panel is a standard useful in a number of molecular assays, calibrated against the 1$^{st}$ WHO International Standard for BK Virus. The EDX BKV Verification Panel includes whole intact virus and is used to measure the presence (qualitative and quantitative) of polyomavirus BK virus DNA. The standards were formulated in negative human plasma and spiked into specimen diluent and was extracted using cobas® 6800/8800 sample preparation workflows. The eluates were run on the LightCycler® 480 Instrument II and tested with dual target mastermix. The BK virus standards were at a concentration ranging from 0.2 IU/rxn to 2×10$^4$ IU/rxn The oligonucleotides specific for BK virus used for this multiplex real-time PCR assay were one oligonucleotide set targeting the VP2 region (SEQ ID NOs:3-5) and one oligonucleotide set targeting the small t-antigen (SEQ ID NOs: 6-8). The probe used in these examples is a TaqMan® probe.

Figure 6:
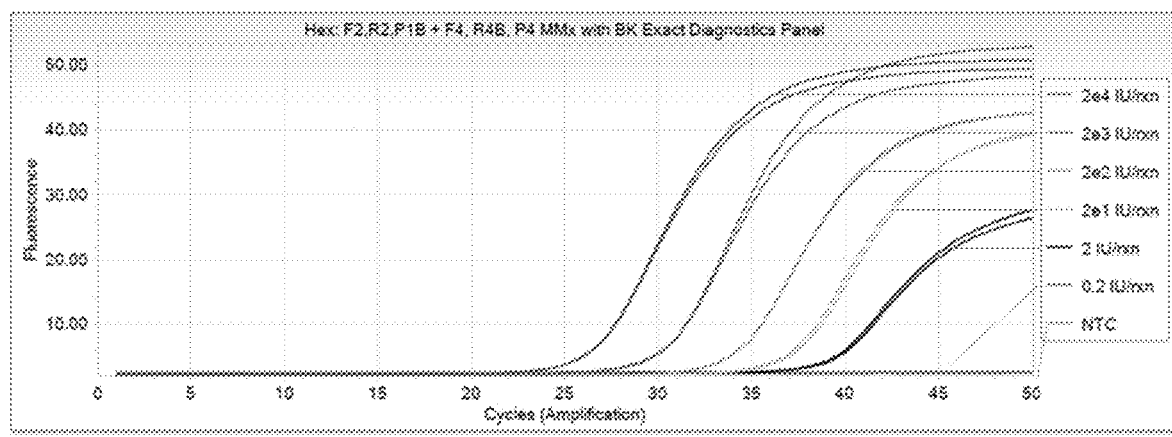
FIG. 6 shows real-time PCR growth curves showing the multiplex detection of BK virus genomic DNA samples using two different sets of oligonucleotide sets (SEQ ID NOs:3-5 and SEQ ID NOs:6-8). Results demonstrate that two sets of oligonucleotides (SEQ ID NOs:3-5 and SEQ ID NOs:6-8) amplify and detect BK virus in a multiplex setting.

The results of the real-time BK virus assay are shown in FIG. 6, which shows real-time PCR growth curves of the dilution panel. These results show that the two sets of oligonucleotides (SEQ ID NOs:3-5 and SEQ ID NOs:6-8) are able to amplify and detect BK virus in a multiplex setting and in a dose-dependent fashion.

Example 6: Dual-Target Multiplex Real-Time BK Virus PCR (SEQ ID NOs:3-5 and SEQ ID NOs:9-11)

The oligonucleotides were tested in a multiplex real-time PCR assay, such that two targets (i.e., "dual target") were tested (i.e., VP2 and small t-antigen). In this test, the BK virus standards were obtained from the Exact Diagnostics BKV Verification Panel (Exact Diagnostics (EDX), Catalog Number BKVP100). The EDX BKV Verification Panel is a standard useful in a number of molecular assays, calibrated against the 1$^{st}$ WHO International Standard for BK Virus. The EDX BKV Verification Panel includes whole intact virus and is used to measure the presence (qualitative and quantitative) of polyomavirus BK virus DNA. The standards were formulated in negative human plasma and spiked into specimen diluent and was extracted using cobas® 6800/8800 sample preparation workflows. The eluates were run on the LightCycler® 480 Instrument II and tested with dual target mastermix. The BK virus standards were at a concentration ranging from 2 IU/rxn to 2×10$^3$ IU/rxn The oligonucleotides specific for BK virus used for this multiplex real-time PCR assay were one oligonucleotide set targeting the VP2 region (SEQ ID NOs:3-5) and one oligonucleotide set targeting the small t-antigen (SEQ ID NOs: 9-11). The probe used in these examples is a TaqMan® probe.

Figure 7:
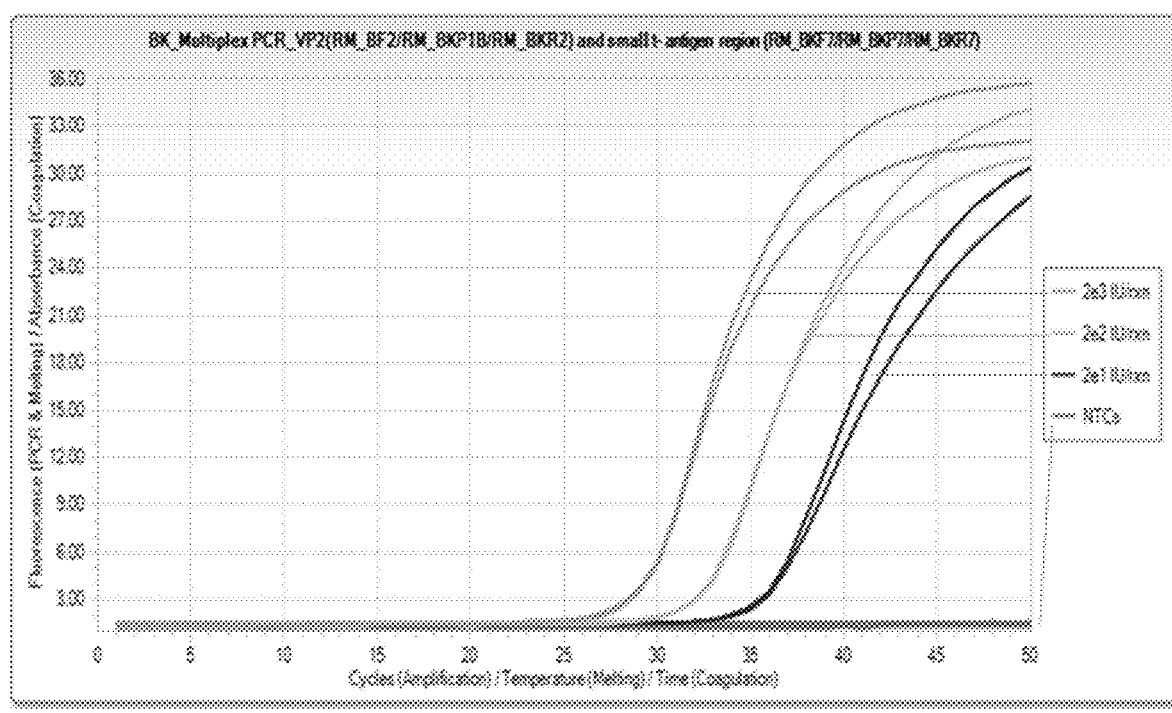
FIG. 7 shows real-time PCR growth curves showing the multiplex detection of BK virus genomic DNA samples using two different sets of oligonucleotide sets (SEQ ID NOs:3-5 and SEQ ID NOs:9-11). Results demonstrate that two sets of oligonucleotides (SEQ ID NOs:3-5 and SEQ ID NOs:9-11) amplify and detect BK virus in a multiplex setting.

The results of the real-time BK virus assay are shown in FIG. 7, which shows real-time PCR growth curves of the dilution panel. These results show that the two sets of oligonucleotides (SEQ ID NOs:3-5 and SEQ ID NOs:9-11) are able to amplify and detect BK virus in a multiplex setting and in a dose-dependent fashion.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of detecting BK virus in a sample, the method comprising: (a) performing an amplifying step comprising contacting the sample with a set of primers to produce an amplification product, if a target nucleic acid of BK Virus is present in the sample; (b) performing a hybridization step comprising contacting the amplification product, if a target nucleic acid is present in the sample, with a probe; and (c) detecting the presence or absence of the amplification product, wherein the presence of the amplification product is indicative of the presence of BK virus in the sample, and wherein the absence of the amplification product is indicative of the absence of BK virus in the sample; wherein the set of primers consists of a first primer consisting of SEQ ID NO:4, and a second primer consisting of SEQ ID NO:5, and wherein the probe consists of SEQ ID NO:3 and optionally a label.

2. The method of claim 1,
wherein the hybridization step comprises contacting the amplification product with the probe, wherein the probe is labeled with a donor fluorescent moiety and a corresponding acceptor moiety;
wherein the detecting step comprises detecting the presence or absence of fluorescence resonance energy transfer (FRET) between the donor fluorescent moiety and the acceptor moiety of the probe; and
wherein the presence or absence of fluorescence is indicative of the presence of absence of BK Virus in the sample.

3. The method of claim 2, wherein the amplification step comprises a polymerase enzyme having 5' to 3' nuclease activity.

4. The method of claim 2, wherein the acceptor moiety is a quencher.

5. The method of claim 1, wherein the sample is a biological sample.

6. The method of claim 5, wherein the biological sample is blood, plasma, or urine.

* * * * *

SEQUENCE LISTING

```
<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (25)..(25)
<223> OTHER INFORMATION: t-Butyl Benzyl-dA

<400> SEQUENCE: 1
cctaactcct caaacatatg ctgta                                          25

<210> SEQ ID NO 2
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (23)..(23)
<223> OTHER INFORMATION: t-Butyl Benzyl-dA

<400> SEQUENCE: 2
acagtggaaa ctttgtgatc cca                                            23
```

```
<210> SEQ ID NO 3
<211> LENGTH: 27
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (17)..(17)
<223> OTHER INFORMATION: 7-deaza-deoxyguanosine

<400> SEQUENCE: 3
attgctggtg ctcctggggc tattgct                                         27

<210> SEQ ID NO 4
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (23)..(23)
<223> OTHER INFORMATION: t-Butyl Benzyl-dA

<400> SEQUENCE: 4
ggctatagct gctataggcc taa                                             23

<210> SEQ ID NO 5
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (28)..(28)
<223> OTHER INFORMATION: t-Butyl Benzyl-dC

<400> SEQUENCE: 5
agtaacagtt tgaattaaag cagcaaac                                        28

<210> SEQ ID NO 6
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (23)..(23)
<223> OTHER INFORMATION: t-Butyl Benzyl-dC

<400> SEQUENCE: 6
agaggaaaat cagcacaaac ctc                                             23

<210> SEQ ID NO 7
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modifed_base
<222> LOCATION: (18)..(18)
<223> OTHER INFORMATION: t-Butyl Benzyl-dC

<400> SEQUENCE: 7
caccctgaca aaggggggc                                                  18
```

```
<210> SEQ ID NO 8
<211> LENGTH: 34
<212> TYPE: DNA
<213> ORGANISM: Artificial Sequence
<220> FEATURE:
<223> OTHER INFORMATION: Probe

<400> SEQUENCE: 8
tgagctactc caggttccaa aatcaggctg atga                              34

<210> SEQ ID NO 9
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (28)..(28)
<223> OTHER INFORMATION: t-Butyl Benzyl-dA

<400> SEQUENCE: 9
cctttacatc ctgctccatt tttttata                                    28

<210> SEQ ID NO 10
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (24)..(24)
<223> OTHER INFORMATION: t-Butyl Benzyl-dA

<400> SEQUENCE: 10
agtgtaagga atttcaccct gaca                                        24

<210> SEQ ID NO 11
<211> LENGTH: 38
<212> TYPE: DNA
<213> ORGANISM: Artificial Sequence
<220> FEATURE:
<223> OTHER INFORMATION: Probe

<400> SEQUENCE: 11
agtattcatt ctcttcattt tatcctcgtc gcccctt                          38
```